(12) United States Patent
Kim

(10) Patent No.: US 9,382,587 B2
(45) Date of Patent: Jul. 5, 2016

(54) DIAGNOSIS OF BREAST CANCER BASED ON EXPRESSION LEVEL OF THIOREDOXIN-1

(75) Inventor: Il Han Kim, Daejeon (KR)

(73) Assignee: PAICHAI UNIVERSITY INDUSTRY-ACADEMIC COOPERATION FOUNDATION, Daejeon (KR)

(*) Notice: Subject to any disclaimer, the term of this patent is extended or adjusted under 35 U.S.C. 154(b) by 6 days.

(21) Appl. No.: 13/560,208

(22) Filed: Jul. 27, 2012

(65) Prior Publication Data
US 2012/0289431 A1 Nov. 15, 2012

Related U.S. Application Data

(63) Continuation-in-part of application No. PCT/KR2011/004729, filed on Jun. 29, 2011, which is a continuation-in-part of application No. 13/257,277, filed as application No. PCT/KR2009/001944 on Apr. 15, 2009.

(30) Foreign Application Priority Data

Mar. 16, 2009 (KR) .................... 10-2009-0022291

(51) Int. Cl.
| | |
|---|---|
| G01N 1/00 | (2006.01) |
| G01N 33/00 | (2006.01) |
| G01N 33/48 | (2006.01) |
| G01N 33/483 | (2006.01) |
| G01N 33/487 | (2006.01) |
| G01N 33/49 | (2006.01) |
| G01N 33/50 | (2006.01) |
| C12Q 1/68 | (2006.01) |
| G01N 33/574 | (2006.01) |

(52) U.S. Cl.
CPC ........ *C12Q 1/6886* (2013.01); *G01N 33/57415* (2013.01); *C12Q 2600/158* (2013.01)

(58) Field of Classification Search
CPC ......... G01N 1/00; G01N 33/00; G01N 33/48; G01N 33/483; G01N 33/4833; G01N 33/487; G01N 33/49; G01N 33/491; G01N 33/50; G01N 33/5002; G01N 33/5005; G01N 33/5091; G01N 33/53; G01N 33/536; G01N 33/574; G01N 33/57407; G01N 33/57415; G01N 2800/00; G01N 2800/56
See application file for complete search history.

(56) References Cited

U.S. PATENT DOCUMENTS

| 2002/0055131 A1 | 5/2002 | Powis |
| 2003/0211624 A1 | 11/2003 | Goldknopf et al. |
| 2007/0105142 A1 | 5/2007 | Wilhelm |
| 2009/0035801 A1 | 2/2009 | Goldknopf et al. |
| 2012/0076731 A1* | 3/2012 | Tabibiazar et al. ............ 424/9.2 |

FOREIGN PATENT DOCUMENTS

| EP | 2 028 492 A1 | 2/2009 |
| KR | 10-2010-0104110 A | 9/2010 |
| WO | 2006/128082 A2 | 11/2006 |

OTHER PUBLICATIONS

David T. Lincoln, et al., The Thioredoxin-Thioredoxin Reductase System . . . , Anticancer Research, vol. 23, No. 3B, pp. 2425-2434, 2003, XP008155195, ISSN: 1109-6535.
Kristina Yeghiazaryan, et al., Irradiated Breast Cancer Patients Demonstrate . . . , Cancer Genomics & Proteomics, International Institute of Anticancer Research, Gr., vol. 4, No. 6, pp. 411-418, 2007, XP008155195, ISSN: 1109-6535.
Y. Matsutani, et al., Inverse Correlation of Thioredoxin Expression With Estrogen . . . , Clinical Cancer Research, The American Association for Cancer Research, vol. 7, No. 11, pp. 3430-3436, 2011, XP008155194, ISSN: 1078-0432.
S.J. Kim, High Thioredoxin Expression Is Associated With Resistance . . . , Clinical Cancer Research, vol. 11, No. 23, pp. 8425-8430, 2005, XP55036040, ISSN: 1078-0432.
Mee-Kyung Cha, et al., Overexpression of Peroxiredoxin I and Thioredoxin 1 in Human Breast Carcinoma, Journal of Experimental & Clinical Cancer Research, Biomed Central Lte, London UK, vol. 28, No. 1, 2009, XP021060930, ISSN: 1756-9966.
Supplementary European Search Report dated Sep. 3, 2012 of the corresponding European Patent Application No. 09841942.7.
Raffel et al., "Increased expression of thioredoxin-1 in human colorectal cancer is associated with decreased patient survival," J. Lab Clin. Med., Jul. 2003, vol. 142, No. 1, pp. 46-51.
Husbeck et al., "The redox protein thioredoxin-1 regulates the constitutive and inducible expression of the estrogen metabolizing cytochromes P450 1B1 and 1A1 in MCF-7 human breast cancer cells," Carcinogenesis, 2002, vol. 23, No. 10, pp. 1625-1630.
Cha et al., "Overexpression of peroxiredoxin I and thioredoxin I in human breast carcinoma," Journal of Experimental & Clinical Cancer Research, 2009, vol. 28, p. 93.
Imai et al., "A proteomics study on human breast cancer cell lines by fluorogenic derivatization-liquid chromatography/tandem mass spectrometry," Biomedical Chromatography, 2008, vol. 22, pp. 1304-1314.
International Search Report dated Apr. 14, 2010 issued in a corresponding PCT International Application No. PCT/KR2009/001944, filed Mar. 16, 2009.

(Continued)

*Primary Examiner* — Alana Harris Dent
(74) *Attorney, Agent, or Firm* — Lucas & Mercanti, LLP

(57) ABSTRACT

The present disclosure relates to a diagnostic marker for breast cancer, having thioredoxin-1 as an active ingredient, and to a diagnostic kit for breast cancer using the same. The thioredoxin-1 is overexpressed in human breast cancer tissue so as to enable the early diagnosis of breast cancer or the early prediction prognosis of breast cancer, and therefore has a valuable use as a diagnostic marker for breast cancer. The present disclosure further relates to a method for the diagnosis of breast cancer comprising measuring serum thioredoxin 1 level. In addition, the method is useful in the early diagnosis of breast cancer thanks to its high diagnostic sensitivity and selectivity.

6 Claims, 12 Drawing Sheets

(56) References Cited

OTHER PUBLICATIONS

International Search Report dated Mar. 20, 2012 issued in a corresponding PCT International Application No. PCT/KR2011/004729, filed Jun. 29, 2011.

Zhang Yan, "The expression of COX-2 and TRX-1 in breast cancer and the correlation with clinicopathologic characteristic and prognosis", Graduation Dissertation, China Medical University (Oct. 30, 2007).

Clark, et al., "Identification of molecules involved in the 'early pregnancy factor' phenomenon," J. Reprod. Fert., vol. 93, pp. 525-539 (1991).

Perkins, et al., "Immunocytochemical Localization of Thioredoxin in Human Trophoblast and Decidua," Placenta, vol. 16, pp. 635-642 (1995).

Office Action dated Feb. 4, 2013 issued in corresponding European Application No. 09841942.9.

D.T. Lincoln, et al; The Thioredoxin-Thioredoxin Reductase System: Over-Expression . . . ; Anticancer Research, 2003, vol. 23, No. 3B; pp. 2425-2434.

\* cited by examiner

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ctgcttttca ggaagccttg                                              20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
tgttggcatg catttgactt                                              20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
agcccggaca atatacacca                                              20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
aatatccacc ttggccatca                                              20

<210> SEQ ID NO 5
```

```
<211> LENGTH: 4
<212> TYPE: PRT
<213> ORGANISM: E.coli

<400> SEQUENCE: 5

Cys Gly Pro Cys
1
```

DIAGNOSIS OF BREAST CANCER BASED ON EXPRESSION LEVEL OF THIOREDOXIN-1

CROSS-REFERENCE TO RELATED APPLICATION

This patent application is a continuation-in-part of PCT/KR2011/004729 filed Jun. 29, 2011 and continuation-in-part of U.S. patent application Ser. No. 13/257,277 filed Sep. 16, 2011, which is a 371 of PCT/KR2009/001944 filed Apr. 15, 2009, which in turn claims the benefit of priority from Korean Patent Application 10-2009-0022291 filed Mar. 16, 2009, the contents of each of which are incorporated herein by reference.

FIELD OF INVENTION

The present invention relates to a diagnostic marker for breast cancer, comprising thioredoxin-1 as an active ingredient, and a diagnostic kit for breast cancer using the same. The present invention further relates to a method for the diagnosis of breast cancer by measuring thioredoxin 1 levels in tissues and blood.

BACKGROUND OF THE INVENTION

Breast cancer is a malignant tumor originating from breast tissue, most commonly from the epithelium lining milk ducts or the lobules that supply the ducts with milk. Breast cancer is reported to occur at a higher rate in women of advanced countries than do other cancers.

Various etiologic factors for breast cancer are now being mentioned, including female hormones, cancer history, family history, lack of having borne a child, dietary habit, etc., without no clear relationship with these has been proven thus far.

In South Korea, breast cancer ranks second after stomach cancer in frequency and fifth after breast cancer, liver cancer, uterine cancer and lung cancer in mortality for women. Breast cancer cases of women in South Korea have rapidly increased every year as have those of Western countries. Recently, breast cancer cases in South Korea are reported to have rapidly increased. A survey report of the Statistics Korea has it that breast cancer cases exceeded uterine cervical cancer cases in 1998 and accounted for 16.1% of women's cancer cases in 2001, ranking first before stomach cancer. In addition, the incident rate of breast cancer was 11.1% between 2001 and 2002, which was greater than that of other cancers. Now, the high incident rate of breast cancer is thought to be associated with various factors. Among them are a low birthrate, breastfeeding for a short period of time, early menarche, late menopause, the westernization of dietary habits, and the pollution of living environment. Further, glandular tissue of women who had been stimulated by female hormones at rapidly increased frequency at the time of their physiologically active change was increased in sensitivity and these individuals may be confronted with a greater likelihood of being struck by breast cancer.

The incidence of breast cancer and the mortality from breast cancer in Korea are expected to increase for a significant period of time in the future in consideration of the trend of because of the westernization of living. As they grow, breast cancer cells, like other cancer cells, generally infiltrate adjacent tissues or metastasize into the lymph nodes. In most breast cancer cases, the patients did not have many detectable symptoms or they did not examine their breasts by themselves. Therefore, it is very important to effectively diagnose early breast cancer to reduce mortality from breast cancer.

To decrease the mortality from breast cancer, early diagnosis is the most important thing. It is also important to do an adjuvant therapy that is suitable in light of the prognosis after the primary initial treatment. For the diagnosis of breast cancer, various methods are used in combination. So far, breast self-examination has accounted for 70% of breast cancer cases. However, it is impossible to discriminate malignant breast tumors from benign tumors by giving breast self-examination. A number of breast cancer screening tests have been employed including X-ray mammography, ultrasound, fine-needle aspiration cytology, and magnetic resonance imaging. Eventually, biopsy is employed to diagnose breast cancer. Mammographic screening for breast cancer uses X-rays to examine the breast. Mammography is effective at determining whether breast tumors are benign or malignant and can detect hidden tumors. This method is one of the most effective techniques by which early breast cancer can be diagnosed before the detection of a lump by breast self-examination. However, mammography is disadvantageous in that diagnostic accuracy is lowered for a breast in which the mammary gland is highly developed or which is a small and dense breast with highly fibrous tissue, like the breasts of young women. In addition, there is a dispute waging about that more frequent mammograms run the risk of significantly increasing breast cancer because of the radiation. As an alternative to mammography, ultrasonography is employed. Ultrasonography can effectively discriminate cystis from lumps, but is ineffective in telling malignant tumors from benign tumors. Ultrasonography can effectively discriminate cystis from lumps, but is ineffective in telling malignant tumors (cancer) from benign tumors (non-cancer). In practical clinics, the finding of abnormalities requires the use of fine-needle aspiration and magnetic resonance imaging for more accurate diagnosis. Even these methods, however, cannot guarantee that malignant tumors (cancer) can be distinguished from benign tumors (non-cancer) although they can reveal morphological differences between normal and abnormal tissues. Ultimately, a biopsy is employed to diagnose breast cancer decisively.

To supplement such breast screening methods, attempts have been made to use blood tumor marker levels to diagnose breast cancer. Although studied for their values as diagnosis or prognosis factors, the application of conventional tumor markers is accompanied by limitations, and there are no officially recommended breast cancer markers.

Thioredoxin (Trx) was discovered as a coenzyme that donates a hydrogen ion to ribonucleotide reductase, an enzyme essential for DNA synthesis in *Escherichia coli*. Characterized by the active site -Cys-Gly-Pro-Cys- (SEQ ID NO: 5) in which the two vicinal cysteine residues interchangeably exist between the oxidized form of a disulfide bond (S—S) and the reduced form of a dithiol (—SH—SH), Trx functions as an intracellular oxidoreduction controller. Thioredoxin (Trx) is a 12 kDa oxidoreductase thatis kept in the reduced state by thioredoxin reductase in a NADPH-dependent reaction. There are two kinds of mammal thioredoxins: thioredoxin 1 (Trx1) and thioredoxin 2 (Trx2). Thioredoxins act as electron donors to peroxidases so that, for example, toxic hydrogen peroxide can be eliminated. Also, thioredoxins provide electrons for ribonucleotide reductase. Thioredoxins plays a role in binding transcription elements to DNA in bacteria while they have an influence on the activity of NF-kB (nuclear transcription factor kB) in eukaryotes. Therefore, thioredoxins are associated with cell death and tumor cells, and play an important role in regulating the growth of tumor cells. Serving as a general disulfide oxidoreductase, thioredoxin facilitates the reduction of other proteins by a redox mechanism based on reversible reduction of a disulfide to two cysteine thiol groups, thereby recovering the normal function of the proteins. In mammalian cells, thioredoxin 1 and 2 are also involved in the regulation of nitric oxide levels and thus in cell death. Therefore, the enzymes are potentially important in conjunction with the onset of many diseases including inflammatory diseases, heart failure, cancer, etc. Immunohistochemical analysis with anti-thioredoxin antibodies revealed the expression of thioredoxins in cancer cells in various tissues such as the liver, colon, pancreas, and the uterine cervix, indicating the implication of thioredoxins in oncogenesis.

There has been a need for a diagnostic marker and a method for breast cancer that allows the accurate diagnosis of early breast cancer and allows the prognosis of breast cancer to be made. Almost few studies have been done on the use of thioredoxin 1 as a diagnostic marker for breast cancer.

SUMMARY OF THE INVENTION

The present invention provides a diagnostic marker for breast cancer, comprising thioredoxin 1 as an active ingredient, and a diagnostic kit for breast cancer, using the same. The present invention also provides a method for diagnosing breast cancer comprising determining the thioredoxin 1 level in tissues and in blood. In addition, the method of the present invention is useful in the early diagnosis of breast cancer due to its high diagnostic sensitivity and selectivity. In one embodiment of the present invention, the blood is serum. Because blood, which is relatively easy to sample, is employed as a specimen, the method for diagnosing breast cancer comprising the thioredoxin 1 level in blood in accordance with the present invention is very simple and does not impose a load on patients compared to conventional methods that are directed to a biopsy.

BRIEF DESCRIPTION OF DRAWINGS

FIG. 10A shows the comparison of serum thioredoxin 1 level in blood samples of normal (N(F/M)) and breast cancer patients (BC) groups. FIG. 10B shows the comparison of serum thioredoxin 1 level in the blood samples of normal (N(F/M)) and lung cancer patients (LC) groups. FIG. 10C shows the comparison of serum thioredoxin 1 level in blood samples of lung cancer patients (LC) and breast cancer patients (BC) groups.

DETAILED DESCRIPTION OF INVENTION

Figure 1:
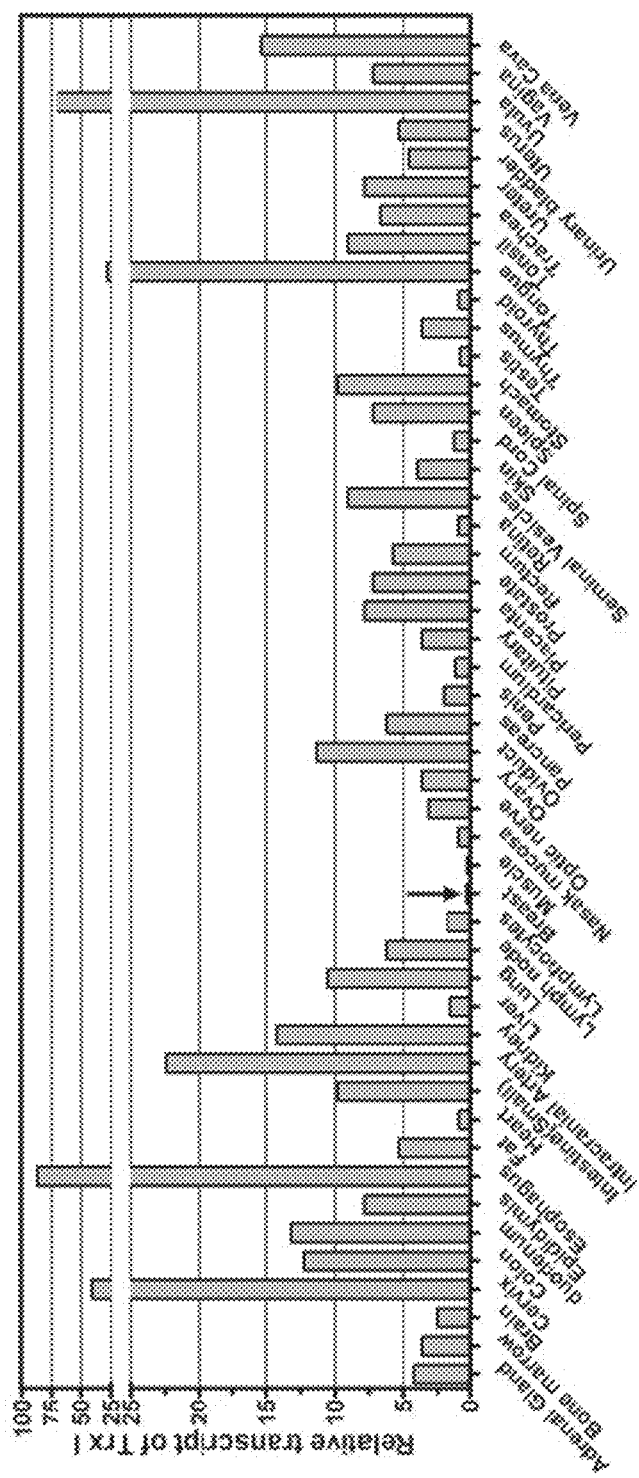
FIG. 1 is a graph showing expression profiles of thioredoxin 1 transcript in 48 different human normal tissues selected from individuals of different ethnicity as measured by 96-well HMRT qPCR assay.

The present invention provides a diagnostic marker for breast cancer, comprising thioredoxin 1 as an active ingredient. Also, the present invention provides a diagnostic kit for breast cancer, comprising an antibody against thioredoxin 1. Furthermore, the present invention provides a method for detecting thioredoxin 1 in breast tissues using an antibody to thioredoxin 1.

In one embodiment, the present invention provides a method for diagnosing breast cancer, comprising the thioredoxin level in tissues or in blood.

In another embodiment of the present invention, the expression levels of thioredoxin 1 in human normal tissue and cancerous tissue were examined. Thioredoxin 1 was found to be expressed at the lowest level in normal breast tissue among 48 different normal human tissues, and at a higher level in breast cancer tissue than in other cancerous tissue, as measured by qRT-PCR and Western blotting. In addition, the more progressed the cancer is, the higher the induction fold of mRNA expression of thioredoxin 1. Thus, the induction fold of mRNA expression of thioredoxin 1 becomes high in stage II~IV breast cancer, particularly stage IV breast cancer, that is, metastatic breast cancer. Further, the induction fold of mRNA expression of thioredoxin 1 is closely associated with the malignancy of cancer as it increases with the progression of cancer. Therefore, the induction fold of mRNA expression of Thoredoxin 1 is associated with subdivision of cancer stages. Found to be overexpressed in human breast cancer tissues, as described above, thioredoxin 1 allows the diagnosis and prognosis of breast cancer and thus is useful as a diagnostic marker for breast cancer.

As elucidated in the Example section below, breast cancer patients were found to have significantly higher serum thioredoxin 1 levels than normal persons, as measured by ELISA. In addition, comparison between breast cancer and other cancers showed that significantly high thioredoxin 1 levels were detected in blood taken from breast cancer patients, compared to patients with other cancers. Moreover, the serum thioredoxin level exhibited a proportional correlation with the progress of breast cancer.

In one embodiment, the present invention provides a method wherein thioredoxin 1 levels in blood samples were measured to detect breast cancer. Because of employing blood as a specimen, it is relatively easy to sample. Therefore, the method for diagnosing breast cancer comprising the thioredoxin level in blood in accordance with the present invention is very simple and does not impose a load on the patients compared to conventional methods which are directed to a biopsy. In addition, the method of the present invention is useful in the early diagnosis of breast cancer thanks to its high diagnostic sensitivity and selectivity.

In another embodiment, the present invention provides a diagnostic kit for breast cancer, comprising an antibody against thioredoxin 1 which can be readily prepared using the markers of the present invention.

The diagnostic kit for breast cancer of the present invention may comprise an antibody specifically binding to thioredoxin 1, a secondary antibody conjugate with a label that can react with a substrate to cause a chromatic change, a substrate solution which develops a color upon reaction with the label, a washing buffer and a reaction stop buffer.

The label conjugated to the secondary antibody is preferably a coloring agent which can bring about a color change as it reacts with its substrate. Representative among them are HRP (horseradish peroxidase), alkaline phosphatase, colloid gold, fluorescein such as FITC (poly L-lysine-fluorescein isothiocyanate) and RITC (rhodamine-B-isothiocyanate), and dye.

As for the substrate solution, it is dependent on the label. Examples include TMB (3,3',5,5'-tetramethyl bezidine), ABTS [2,2'-azino-bis(3-ethylbenzothiazoline-6-sulfonic acid)], and OPD (o-phenylenediamine). The coloring substrate is preferably provided in the form of a solution in buffer (0.1M NaOAc, pH 55).

Preferably, phosphate buffer, NaCl and Tween 20 are contained in the washing solution. More preferable is a solution (PBST) containing 0.02M phosphate buffer, 0.13M NaCl, and 0.05% Tween 20. After the antibody is allowed to react with the antigen, the antigen-antibody complex is treated with the secondary antibody conjugate, followed by immobilization and then washing 3~6 times with the washing solution. A sulfuric acid solution ma be used to stop the enzymatic reaction.

Hither expression levels of thioredoxin 1 are detected in stage II~IV breast cancer tissues than in stage I breast cancer or normal breast tissues.

Examples of the immobilizer include a nitrocellulose membrane, a PVDF (polyvinylidene difluoride) membrane, a 96-well plate formed of polyvinyl resin or polystyrene resin, and a slide glass.

The antigen-antibody binding reaction may be assayed using a typical method such as ELISA, radioimmunoassay (RIA), sandwich assay, Western blotting, immunoprecipitation immunohistochemical staining, immunofluorescence assay, enzyme-substrate coloring assay, and antigen-antibody aggregation.

In accordance with one embodiment of the present invention, the diagnosis or prognosis of breast cancer can be readily predicted with high accuracy by detecting the breast cancer marker with an antigen-antibody reaction using an antibody specifically binding to thioredoxin 1. For example, a protein preparation containing thioredoxin 1 is separated on SDS-PAGE, and transferred and fixed onto an immobilizer which is then treated with an antibody against thioredoxin 1 to determine the expression level of thioredoxin 1. That is, when the expression level of thioredoxin 1 in the breast tissue of interest is measured, the breast tissue is diagnosed with cancer or predicted to become cancerous when the thioredoxin 1 expression level is higher than that of normal breast tissue.

INDUSTRIAL APPLICABILITY

As described hitherto, the method based on thioredoxin 1 level in accordance with the present invention is convenient in diagnosing breast cancer because thioredoxin 1 is a useful marker for the early diagnosis of breast cancer thanks to its high sensitivity and specificity.

EXAMPLE

A better understanding of the present invention may be obtained through the following examples which are set forth to illustrate, but are not to be construed as limiting the present invention.

Example 1 qRT-PCR Assay

For expression profiling of human target genes, qRT-PCR (Quantitative real-time Polymerase Chain Reaction) arrays were used to conduct the following reactions.

Human Major 48 tissues real-time (HMRT) qPCR arrays, Cancer Survey real-time (CSRT 96-I) qPCR arrays, and Human Breast Cancer real-time (BCRT I-V) qPCR arrays, all purchased from OriGene (OriGene Technologies, Inc, Rockville, Md., USA) were used. Simultaneous examination of the expression of target genes in 48 different tissues was performed using the HMRT array, which consisted of panels of first-strand cDNA from human tissues selected from individuals of different ethnicity. Expression levels of target genes in eight different cancers (breast, colon, kidney, liver, lung, ovary, prostate, and thyroid) were measured using the CSRT array consisting of 12 samples from each cancer type with cancer stages varying from I to IV. Expression of target genes in breast cancer was examined using four different sets of arrays (BCRT I-IV) for 192 test samples and using the CSRT 96-I array for 12 test samples. In the 204 samples, cancer grading was distributed as follows: 19 as stage 0 (normal); 37 as stage I; 76 as stage II; 60 as stage III; and 12 as stage IV. The cancer tissue types consisted of ductal (n=154), lobular (n=13), metastatic (n=12), and other histological types of cancer (n=25), including medullary, mucinous, tubular, recurrent, and papillary. More clinicopathological information for each patient is described in OriGene's product sheet.

PCR was performed in 96-well optical plates using iCycler (Bio-Rad Laboratories, Hercules, Calif., USA) with primers specific for Trx1, Trx2, β-actin, GAPDH (glyceraldehyde 3-phosphate dehydrogenase), and iQ SYBR Green Supermix (Bio-Rad). The resulting fluorescence proportional to the amount of amplified DNA was measured at the end of each elongation phase at 530 nm. A standard graph of $C_T$ (the point at which the fluorescence crosses the threshold) values obtained from serially diluted target genes was constructed for all reactions to ensure that they were amplified and reported in proportion to the template. $C_T$ values were converted to gene copy number of the template cDNA using the equation $2^{\Delta\Delta C_T}$. The $\Delta C_T$ is the abundance of cDNAs for transcripts of each gene normalized to the β-actin and GAPDH at each time point. The $\Delta\Delta C_T$ is obtained by subtracting a calibrator value for each gene transcript being assayed. In parallel with each cDNA sample, standard curves were constructed to correlate $C_T$ values using serial dilutions of the target gene. The property of the standard curve was evaluated from the slope and the correlation coefficient. Quantification was performed by comparing the fluorescence of a PCR product of unknown concentration with the fluorescence of several dilutions. Melting curve analysis was used for product validation. The primers for β-actin and GAPDH were purchased from Origene. Other primer sequences are summarized in Table 1.

TABLE 1

| Sequence of Primers for Real-Time PCR Amplification | Direction | Primer Sequence (5'->3') |
|---|---|---|
| Human thioredoxin 1 (Trx 1) | Forward | ctgcttttcaggaagccttg |
|  | Referse | tgttggcatgcatttgactt |
| Human thioredoxin 2 (Trx 2) | Forward | agcccggacaatatacacca |
|  | Reverse | aatatccaccttggccatca |

1-1. Transcript Level of Thioredoxin 1 in 48 Different Normal Human Tissues

Transcript levels of thioredoxin 1 in 48 different human normal tissues selected from individuals of different ethnicities were determined using 96-well HMRT qPCR arrays, and the results are given in FIG. 1.

As can be seen in FIG. 1, thioredoxin 1 was expressed at the lowest level ($0.24 \times 10^{-4}$ pg) in breast tissue among the 48 major human tissues.

1-2. Levels of mRNA of Thioredoxin 1 and 2 in Human Solid Cancerous Tissues

The expression profiles of thioredoxin 1 and 2 in eight solid cancers (breast, colon, kidney, liver, lung, ovary, prostate, and thyroid) were made using the CSRT 96-I array.

Figure 2:
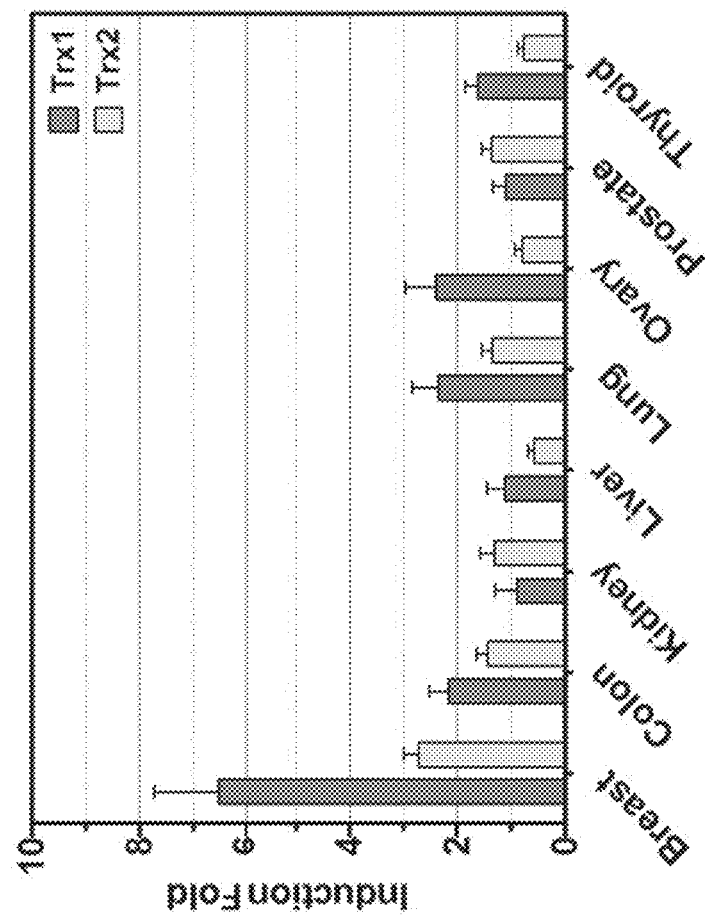
FIG. 2 is a graph showing mRNA levels of thioredoxin 1 and 2 in eight solid cancers (breast, colon, kidney, liver, lung, ovary, prostate, and thyroid) as measured by CSRT 96-I arrays.

The results are given in FIG. 2.

As shown in FIG. 2, thioredoxin 1 was expressed at the highest level in breast cancer (6.47±1.22) among the eight solid cancers, whereas thioredoxin 2 was not preferentially expressed in breast cancer (2.72±0.28) ($P=0.0067$).

1-3. Levels of mRNA of Thioredoxin 1 and 2 in Human Breast Cancerous Tissues

To examine the expression profile of thioredoxin 1 in breast cancer, the mRNA levels of thioredoxin 1 and 2 in breast cancer were quantified using a 48-well BCRT II array. The induction fold was obtained from the mRNA concentrations of thioredoxin 1 and 2.

Figure 3:
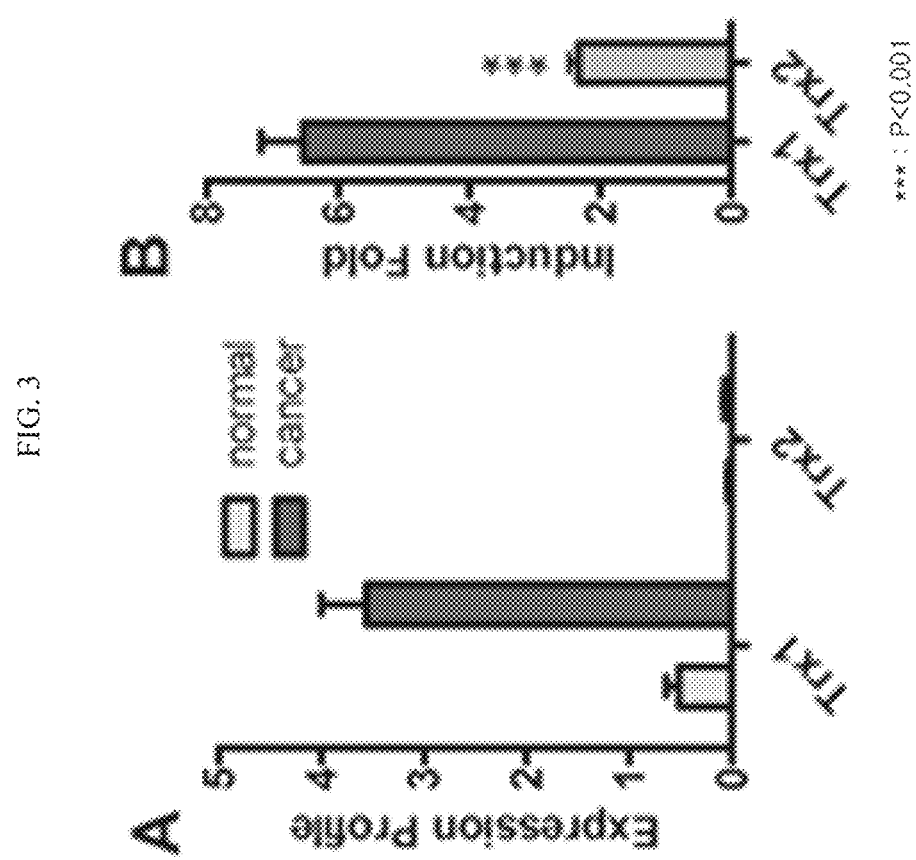
FIG. 3 is of graphs showing mRNA levels of thioredoxin 1 and 2 in breast cancer (A) and levels of induction fold obtained therefrom (B).

The mRNA concentrations (A) of thioredoxin 1 and 2 in breast cancer and the induction folds obtained therefrom are shown in FIG. 3.

As can be seen in FIG. 3, the mRNA levels of thioredoxin 1 were much higher than those of thioredoxin 2 in both normal breast and breast cancer tissues. Also, the higher-induction fold of thioredoxin in malignant tissue is depicted compared with thioredoxin 2.

1-4. Correlation Between Grade of Human Breast Cancer and Thioredoxin 1

To evaluate the correlation of thioredoxin with the progression of breast cancer, mRNA levels in 204 samples of normal and malignant breast tissues ranging from 0 to IV grade were assessed using five different sets of qRT-PCR arrays [Cancer Survey real-time (CSRT 96-I) qPCR array (n=9), and human breast cancer real-time (BCRT I-V) qPCR array I-V (n=1176)], the induction fold from normal (grade 0) to malignant (grade I, II, III, IV) was determined.

Figure 4:
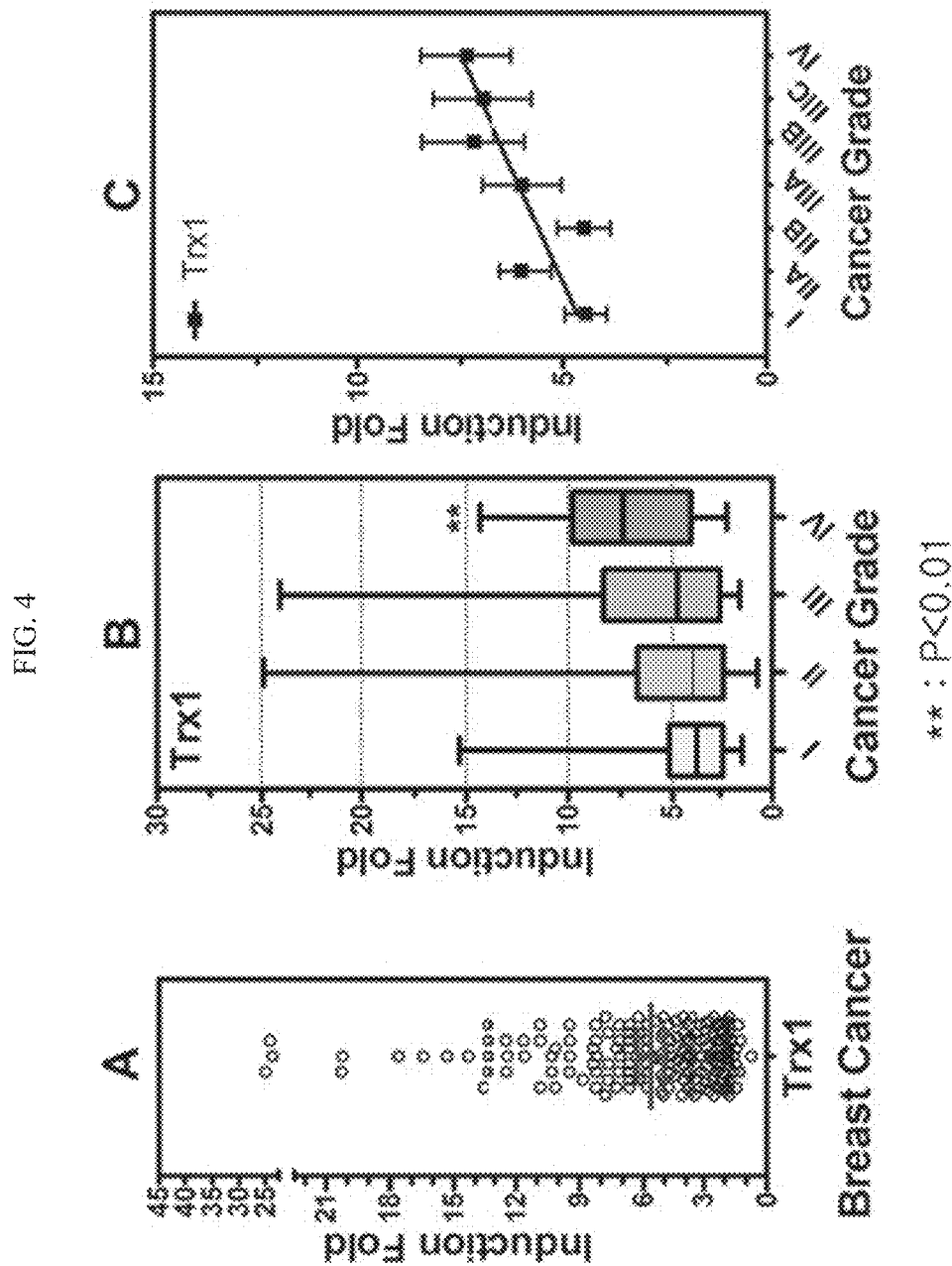
FIG. 4 shows the induction fold of mRNA expression of thioredoxin 1 in human breast cancer as a scatter dot plot (A), the correlation between the mRNA expression of thioredoxin 1 and the progression of cancer as a box-and-whisker plot (B), and the induction fold of mRNA expression of thioredoxin in subdivided cancer (stage I, IIA, IIB, IIIA, IIIB, IIIC and IV) as a plot (C).

In FIG. 4, Induction fold data for mRNA expression of thioredoxin 1 in human breast cancer were displayed as a scatter dot plot (A), the correlation of mRNA expression of thioredoxin with cancer grade was represented as box-and-whisker plots (B), and data for the induction fold of mRNA expression of thioredoxin 1 in subdivided human breast cancer (stage I, IIA, IIB, IIIA, IIIB, IIIC, and IV) was plotted (C).

In breast cancer, as can be seen in FIG. 4, 2-fold overexpression of thioredoxin 1 occurred in 168 of 185 cases (90.8%). Mean±SEM induction fold was 5.64±0.33 for thioredoxin 1 (A). There was a significant correlation between the induction fold of thioredoxin 1 and increasing cancer grade. The higher the grade of cancer, the higher the induction fold of mRNA expression of thioredoxin 1. The induction fold was closely correlated with stage II~IV breast cancer, especially stage IV cancer, that is, metastatic cancer (B). Further, induction fold was associated with subdivisions of cancer stages ($P=0.0191$) (C).

Example 2

Western Blotting Analysis

To examine the expression level of thioredoxin 1 in human breast cancer tissues with Western blotting analysis, the forowing experiment was conducted.

Total membrane and soluble proteins from clinically defined human cancer and normal tissues were obtained from Capital Biosciences (Gaithersburg, Md., USA). Proteins from different individuals and matched paired individuals (normal tissue and primary cancers; primary and metastatic cancers) were used for immunological analysis. The clinical and pathological traits of the cancers are summarized in Table 2, below.

The total membrane and soluble protein lysates (15 μg) from seven cancer tissue types (brain, breast, colon, kidney, liver, lung, and ovary) were loaded into reducing and non-reducing SDS-PAGE, followed by Western blot analysis using an Amersham ECL Western blotting system (GE Healthcare, Chalfont St. Giles, United Kingdom). Anti-thioredoxin 1, and anti-copper/zinc (Cu/Zn) superoxide dismutase (SOD) rabbit polyclonal antibodies that have cross-reactivity with the corresponding human protein were purchased from AbFrontier (Seoul, Korea). Samples were fractionated by electrophoresis on a 4% to 20% gradient SDS-PAGE (GenScript Corp., Piscataway, N.J., USA) and transferred onto PVDF (polyvinylidene difluoride) membranes (Millipore, Billerica, Mass., USA). The membranes were blocked and incubated at room temperature for 2 hours with an antibody (1:1000 by volume) in PBS containing 0.1% Tween 20. After washing many times, the membranes were incubated with horseradish peroxidise-conjugated polyclonal goat anti-rabbit IgG antibody (1:2000 by volume). Then, the membranes were washed in PBS, and the chemiluminescent substrate was added. The membranes were stained with Coomassie Blue R-250 for verification of the loading sample.

TABLE 2

| Sample | Tissue | Appearance | Age/Gender | Diagnosis |
|---|---|---|---|---|
| BRN0 | Brain | Normal | 26/M | Normal |
| BRC0 | Brain | Tumor | 40/M | Astrocytoma |

TABLE 2-continued

| Sample | Tissue | Appearance | Age/Gender | Diagnosis |
|---|---|---|---|---|
| BEN0-4 | Breast | Normal | 82/F. 45/F. 56/F. 64/F. 76/F | Normal |
| BEC0 | Breast | Tumor | 47/F | Medullary Carcinoma, Well Differentiated |
| BEC1 | Breast | Tumor | 40/F | Invasive Lobular Carcinoma |
| BEC2 | Breast | Tumor | 42/F | Adenocarcinoma, Moderately Differentiated |
| BEC3 | Breast | Tumor | 42/F | Fibroadenoma |
| BEC4 | Breast | Tumor | 50/F | Infiltrative Ductal Carcinoma |
| CLN0 | Colon | Normal | 60/F | Normal |
| CLC0 | Colon | Tumor | 48/M | Adenocarcinoma, Well Differentiated |
| KDN0 | Kidney | Normal | 83/F | Normal |
| KDC0 | Kidney | Tumor | 43/F | Granular Cell Carcinoma, |
| LVN0 | Liver | Normal | 30/M | Normal |
| LVC0 | Liver | Tumor | 65/M | Hepatic Cellular Carcinoma, |
| LUN0-4 | Lung | Normal | 24/F. 26M. 66/M. 71/M. 76/F | Normal |
| LUC0 | Lung | Tumor | 72/M | Squamous Cell Carcinoma |
| LUC1 | Lung | Tumor | 33/M | Squamous Cell Carcinoma, Moderately Differentiated |
| LUC2 | Lung | Tumor | 51/F | Adenocarcinoma, Moderately Differentiated |
| LUC3 | Lung | Tumor | 58/M | Squamous Cell Carcinoma, Moderately Differenciated |
| LUC4 | Lung | Tumor | 61/M | Adenocarcinoma |
| OVN0-4 | Ovary | Normal | 74/F. 37/F. 62/F. 69/F. N/A/F | Normal |
| OVC0 | Ovary | Tumor | 51/F | Cystoadenocarcinoma |
| OVC1 | Ovary | Tumor | 42/F | Granular Cell Carcinoma |
| OVC2 | Ovary | Tumor | 51/F | Cystoadenoma |
| OVC3 | Ovary | Tumor | 57/F | Leiomyosarcoma, Well Differentiated |
| OVC4 | Ovary | Tumor | Adult/F | Clear Cell Adenocarcinoma |
| BE1N | Breast | Adjacent Normal | 70/F, same patient | Normal |
| BE1P | Breast | Primary Tumor | | Invasive Ductal Carcinoma |
| BE2P | Breast | Primary Tumor | 59/F, same patient | Breast Carcinoma |
| BE2M | Breast | Metastatic Tumor | | Breast Tumor Metastasized to Lung |
| CL1N | Colon | Adjacent Normal | 62/F, same patient | Normal |
| CL1P | Colon | Primary Tumor | | Adenocarcinoma |
| CL2P | Colon | Primary Tumor | 66/F, same patient | Adenocarcinoma |
| CL2M | Colon | Metastatic Tumor | | Colon Tumor Metastasized to Lymph Node |
| LU1N | Lung | Adjacent Normal | 46/M, same patient | Normal |
| LU1P | Lung | Primary Tumor | | Squamous Cell Carcinoma |
| LU2P | Lung | Primary Tumor | 75/M, same patient | Squamous Cell Carcinoma |
| LU2M | Lung | Metastatic Tumor | | Lung Tumor Metastasized to Lymph Node |

Figure 5:
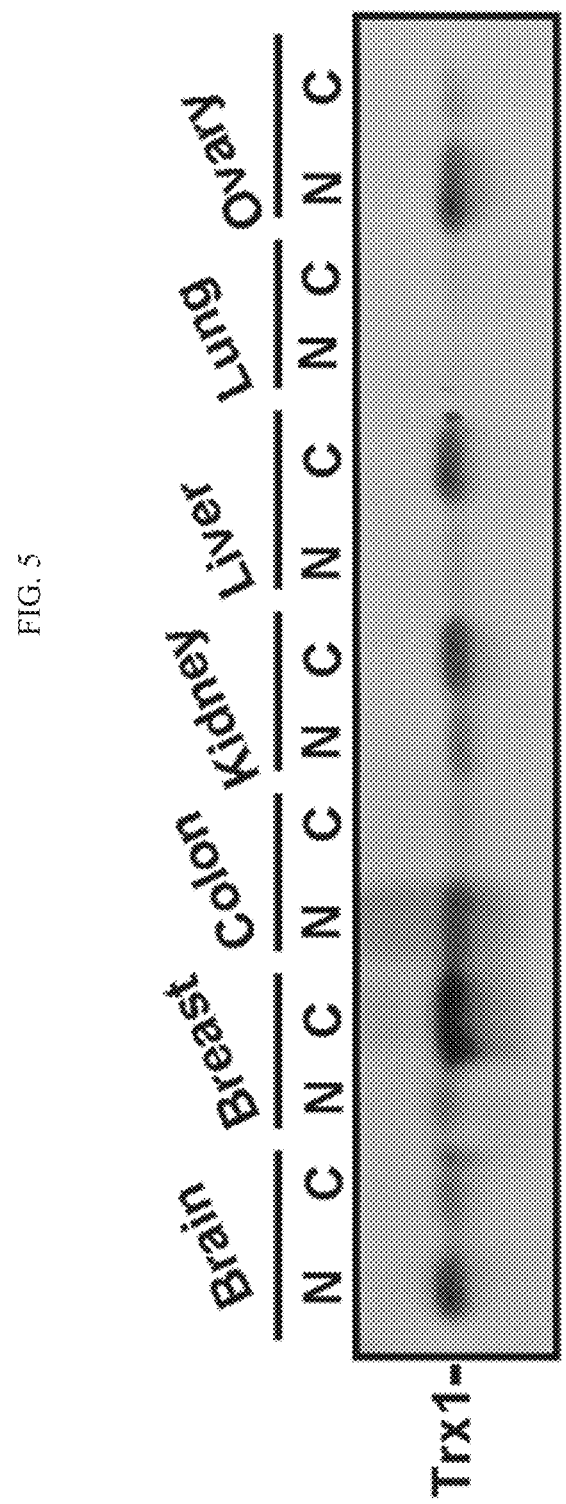
FIG. 5 shows the expression level of thioredoxin 1 in human breast cancerous tissues as measured by Western blot assay.

The results are shown in FIG. 5.

As shown in FIG. 5, thioredoxin 1 was expressed at the highest level in human breast cancerous tissues.

2-1. Expression Levels of Thioredoxin 1 in Human Normal Tissues and Cancerous Tissues (Breast, Lung, Ovary)

The expression levels of thioredoxin 1 in four normal tissues and four cancerous tissues from different individuals were analyzed by Western blotting.

Figure 6:
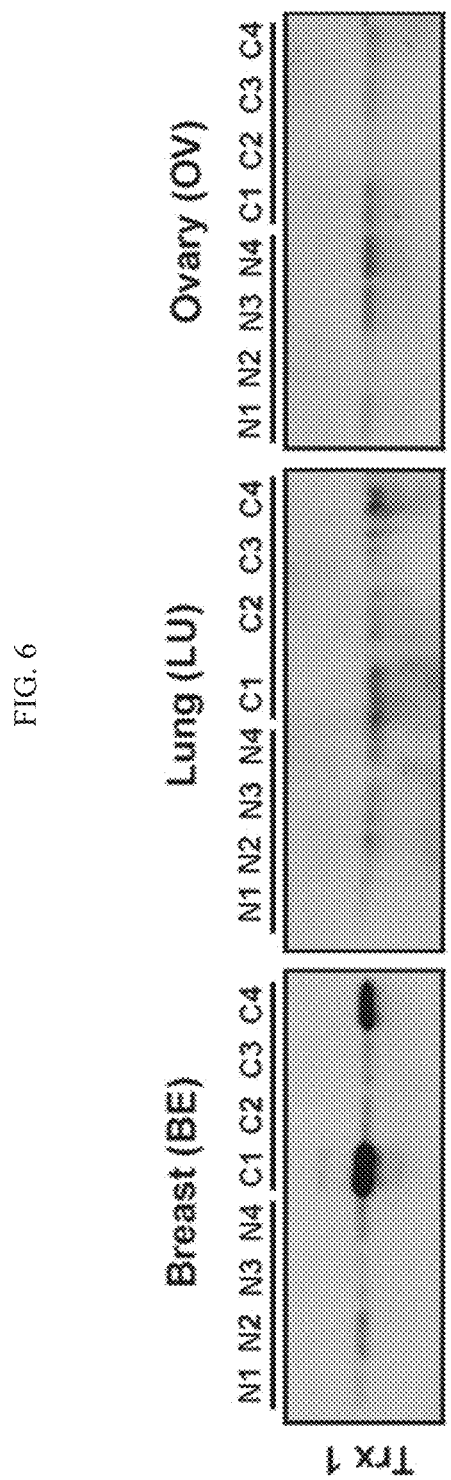
FIG. 6 shows the expression levels of thioredoxin 1 in four normal tissues and four cancerous tissues from different individuals, as measured by Western blotting assay.

The results are given in FIG. 6.

As can be seen in FIG. 6, thioredoxin 1 was overexpressed in breast cancer.

2-2. Expression Levels of Thioredoxin 1 in Paired Sets of Breast Tissue and Paired Sets of Other Tissues (Lung and Colon)

The expression levels of thioredoxin 1 in the paired sets of breast tissue (paired normal and primary cancer from the same individual; paired primary and metastatic cancer from the same individual) and the paired sets of other tissues (lung and colon) were analyzed by Western blotting. Cu/Zn SOD is used as positive control.

Figure 7:
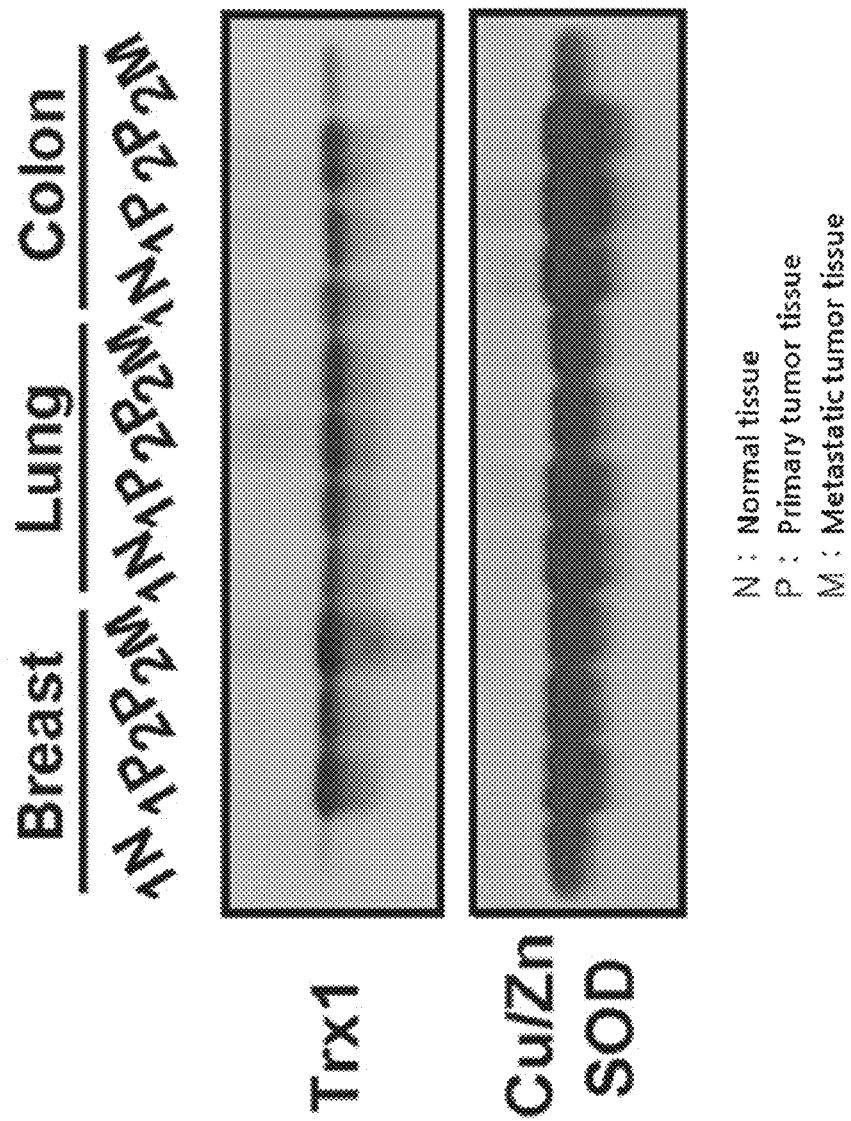
FIG. 7 shows the expression levels of thioredoxin 1 in paired sets of breast tissue (paired normal and primary cancer from the same individual; paired primary and metastatic cancer from the same individual) and paired sets of other cancerous tissues (lung and colon), as measured by Western blotting assay.

The results are shown in FIG. 7.

As can be seen in FIG. 7, thioredoxin 1 was preferentially overexpressed in breast cancer tissues over the other tissues.

Example 3

Subjects

All sera of normal persons (control) and lung cancer patients were obtained from white Caucasians. To make them suitable for a biomarker study, all the sera were collected and treated according to the instructions of the FDA (Food and Drug Administration) and the NCI (National Cancer Institute). They were prepared from the blood collected after the approval of the IRB and the HIPAA. All the sera and the clinical information thereof were provided from Asterand (U.S.A.) and Bioserve (U.S.A.) as summarized in Tables 3 and 4, below.

TABLE 3

| Age | Type of BC | Stage(S) | S Group |
|---|---|---|---|
| 65 | Infiltrating lobular | T1cN0M0 | I |
| 56 | Invasive lobular | T1N0MX | I |
| 77 | Invasive lobular | T1N0M0 | I |
| 54 | Lobular | T1bNXM0 | I |
| 48 | Lobular | T1bNXM0 | I |
| 37 | Lobular | T1cN0M0 | I |
| 77 | Lobular | T1cNXMX | I |
| 33 | Infiltrating lobular | T1cN0M0 | I |
| 49 | Lobular | T1cN0M0 | I |
| 63 | Infiltrating ductal | T1bN0MX | I |
| 37 | Infiltrating ductal | T1cN0M0 | I |
| 55 | Infiltrating ductal | T1N0M0 | I |
| 75 | Infiltrating ductal | T1NXM0 | I |
| 57 | Infiltrating ductal | T1bNXM0 | I |
| 75 | Infiltrating ductal | T1bN0MX | I |
| 47 | Infiltrating ductal | T1cN0MX | I |
| 50 | Infiltrating ductal | T1cN0MX | I |
| 35 | Infiltrating ductal | T1cNXM0 | I |
| 83 | Infiltrating ductal | T1N0M0 | I |
| 87 | Infiltrating ductal | T1NXM0 | I |
| 65 | Infiltrating lobular | T1cN1M0 | IIA |
| 42 | Invasive lobular | T2NXMX | IIA |
| 36 | Lobular | T2N1MX | IIB |
| 91 | Lobular | T3N0MX | IIB |
| 79 | Lobular | T2NXM0 | IIA |
| 43 | Lobular | T2NXM0 | IIA |
| 34 | Lobular | T1cN1M0 | IIA |
| 73 | Lobular | T1cN1M0 | IIA |
| 28 | Lobular | T2NXM0 | IIA |
| 55 | Lobular | T2NXM0 | IIA |
| 54 | Lobular | T1cN1M0 | IIA |
| 28 | Lobular | T1cN1M0 | IIA |
| 65 | Infiltrating ductal | T1cN1M0 | IIA |
| 33 | Infiltrating ductal | T2N0M0 | IIA |
| 48 | Infiltrating ductal | T2N0MX | IIA |
| 58 | Infiltrating ductal | T2N1M0 | IIB |
| 81 | Infiltrating ductal | T2N1M0 | IIA |
| 83 | Infiltrating ductal | T2N1M0 | IIB |
| 73 | Infiltrating ductal | T2N0MX | IIA |
| 48 | Infiltrating ductal | T2N0MX | IIA |
| 52 | Infiltrating ductal | T2NXM0 | IIA |
| 72 | Infiltrating ductal | T2NXM0 | IIA |
| 33 | Infiltrating ductal | T2N0M0 | IIA |
| 69 | Infiltrating lobular | T2N2M0 | IIIA |
| 42 | Lobular | T2N2MX | IIIA |
| 83 | Lobular | T4N0M0 | IIIB |
| 26 | Lobular | T2N2M0 | IIIA |
| 79 | Lobular | T4N2M0 | IIIB |
| 57 | Lobular | T4bN0M0 | IIIB |
| 44 | Lobular | T3N2MX | IIIA |
| 73 | Lobular | T4bN1M0 | IIIB |
| 55 | Lobular | T2N2M0 | IIIA |
| 66 | Invasive Ductal | T2N2M0 | IIIA |
| 73 | Infiltrating ductal | T2N2M0 | IIIA |
| 53 | Infiltrating ductal | T3N2M0 | IIIA |
| 46 | Infiltrating ductal | T1N2M0 | IIIA |
| 76 | Infiltrating ductal | T3N2M0 | IIIA |
| 52 | Infiltrating ductal | T3N1M0 | IIIA |
| 44 | Infiltrating ductal | T2N2M0 | IIIA |

All are from female Caucasian patients

TABLE 4

| Characteristics | No. of samples |
|---|---|
| Breast Carcinoma | 59 |
| Female | 59 |
| Mean age (years) | 57.16 ± 17.33 (26-91) |
| Stage I | 20 |
| Stage II | 23 (IIA 19, IIB 4) |
| Stage III | 16 (IIIA 12, IIIB 4) |
| Lobular Carcinoma of the Breast | 30 |
| Ductal Carcinoma of the Breast | 29 |
| Non-small Cell Lung Cancer (NSCLC) | 111 |
| Male | 50 |
| Female | 61 |
| Mean age (years) | 41 ± 10.39 (41-85) |
| Stage I | 39 (IA 19, IB 20) |
| Stage II | 32 (IIA 16, IIB 16) |
| Stage III | 30 (IIIA 21, IIIB 90) |
| Stage IV | 10 |
| Colorectal Carcinoma | 61 (Rectal 14) |
| Male | 33 (Rectal 7) |
| Female | 31 (Rectal 7) |
| Mean age (years) | 63.84 ± 12.20 (39-38) |
| Stage I | 6 |
| Stage II | 36 (Rectal 7) |
| Stage III | 22 (Rectal 7) |
| Kidney Carcinoma | 30 |
| Male | 17 |
| Female | 13 |
| Mean age (years) | 55.07 ± 11.22 (34-76) |
| Stage I | 26 |
| Stage II | 4 |
| Normal Control | 100 |
| Male | 50 |
| Female | 50 |
| Male Mean age (years) | 44.54 ± 14.85 (20-76) |
| Female Mean age (years) | 43.70 ± 14.95 (18-71) |
| Male/Female Mean age (years) | 44.12 ± 14.83 (18-76) |

*All serums are from white Caucasian.

Example 4

ELISA Assay

ELISA (Enzyme-linked immunosorbent assay) was performed to quantitatively analyze blood proteins.

Sera obtained after the centrifugation of blood samples taken from normal persons and breast cancer patients were used for quantitative protein analysis with an ELISA kit using antibodies of interest (Express ELISA kit (rabbit), GenScript). In this regard, mono-specific antibodies to respective antigens were obtained by injecting purified peptides into rabbits to form antisera and purifying the antisera on a Protein A column.

A standard curve was made from the absorbance at 450 nm of various concentrations of each antigen peptide. Serum protein levels were determined with reference to the standard curve from the mean values of three measurements of absorbance at 450 nm. For statistical analysis, the software GraphPad Prism (ver. 5.04) (GraphPad Software) was used.

4-1: Measurement of Serum Thioredoxin 1 Level in Breast Cancer Patients

Figure 8:
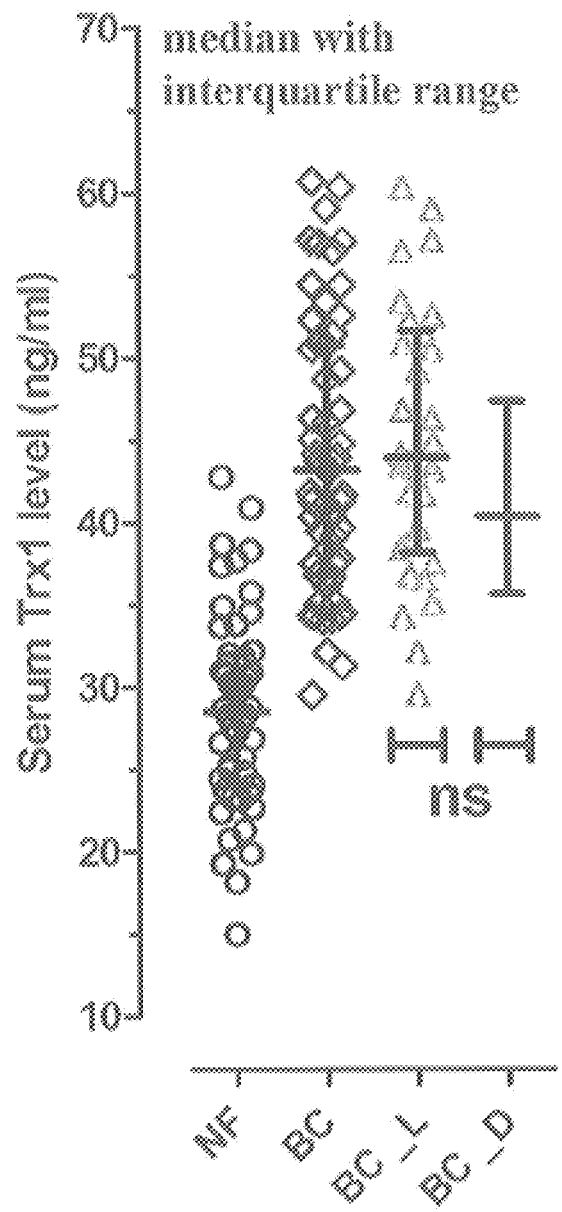
FIG. 8 shows serum thioredoxin 1 levels in normal control and breast cancer patient groups, as measured by ELISA.

Measurements of the ELISA performed on the sera of 50 normal female persons and 59 breast cancer patients over a wide range of ages (41-85) with a uniform distribution (41±10.39, mean±SD) were subjected to ROC curve analysis and the results are shown in FIG. 8 and Table 5.

TABLE 5

|  | Normal Control | | | | Breast Cancer | | | | | KC | (ng/ml of serum) LC | CRC |
| --- | --- | --- | --- | --- | --- | --- | --- | --- | --- | --- | --- | --- |
|  | F/M | F | M | I-III | I | II | III | L | D | (I/II) | (I-IV) | (I-III) |
| # of values | 100 | 50 | 50 | 59 | 20 | 23 | 16 | 30 | 29 | 30 | 111 | 64 |
| 75% Percentile | 23.26 | 23.98 | 22.35 | 36.84 | 34.27 | 36.14 | 40.73 | 38.18 | 35.65 | 25.79 | 25.23 | 27.71 |
| Median | 27.64 | 28.50 | 26.22 | 43.21 | 38.64 | 43.48 | 46.19 | 43.94 | 40.37 | 30.96 | 31.89 | 31.09 |
| 75% Percentile | 31.96 | 32.04 | 31.97 | 50.76 | 44.65 | 51.43 | 53.16 | 51.64 | 47.39 | 35.54 | 37.84 | 38.29 |
| Mean | 27.93 | 28.62 | 27.24 | 43.77 | 40.10 | 44.36 | 47.53 | 45.09 | 42.41 | 31.12 | 31.71 | 32.92 |
| Std. Deviation | 6.113 | 6.054 | 6.155 | 8.182 | 6.551 | 8.727 | 7.695 | 8.168 | 8.112 | 7.541 | 8.254 | 7.864 |
| Std. Error | 0.611 | 0.856 | 0.871 | 1.065 | 1.465 | 1.82 | 1.924 | 1.491 | 1.506 | 1.377 | 0.784 | 0.991 |
| Lower 95% CI | 26.72 | 26.90 | 25.49 | 41.64 | 37.03 | 40.58 | 43.43 | 42.04 | 39.33 | 28.31 | 30.16 | 30.94 |
| Upper 95% CI | 29.14 | 30.34 | 28.99 | 45.91 | 43.17 | 48.13 | 51.63 | 48.14 | 49.50 | 33.94 | 33.26 | 34.9 |

As shown in FIG. 8 and Table 5, the mean value of serum thioredoxin levels was detected at 28.62±6.054 ng/mL in the female normal control (NF), and at 43.77±8.182 ng/mL in the breast cancer group (BC), with about a 53% increase compared to the normal control. With reference to the serum level of thioredoxin 1 according to sub-type of breast cancer, it was 45.09±8.168 in lobular carcinoma of breast (BC_L) and 42.41±8.112 in ductal carcinoma of breast (BC_D). The serum thioredoxin 1 level in lobular carcinoma of breast was about 6.3% increased compared to that in ductal carcinoma of breast.

In addition, measurements of serum thioredoxin 1 levels in the female normal control (n=50) and the breast cancer group (n=59) were subjected to ROC curve analysis, and the results are summarized in Table 6.

In addition, measurements of blood thioredoxin 1 levels were subjected to ROC curve analysis and the results are summarized in Table 6.

As can be seen in Table 6, when compared to the female normal control (NF, n=50) and the male normal control (NM, n=50), the cut-off value for breast cancer was detected at >33.8179 ng/mL, with a sensitivity of 94.9% and a specificity of 83.0%.

4-3. Analysis of Thioredoxin 1 as Breast Cancer-Specific Marker

To examine the selectivity of the blood marker thioredoxin 1 for breast cancer, the data of serum thioredoxin 1 levels for breast cancer in comparison to other cancers of Example 4-2 (lung cancer (LC), kidney cancer (KC) and colorectal cancer

TABLE 6

| Type of Cancer | AUC* (±SEM) | Sensitivity (%) | Specificity (%) | Trx1 Cut-off Value (ng/ml) | # of serum (Grade) |
| --- | --- | --- | --- | --- | --- |
| Breast(F) | 0.941 ± 0.0205 | 94.9 | 82.0 | >33.8179 | 59 (I/II/III) |
| Breast(F/M) | 0.947 ± 0.0155 | 94.9 | 83.0 | >33.8179 | 59 (I/II/III) |
| Colorectal | 0.687 ± 0.0425 | 68.3 | 61.0 | >29.0533 | 64 (I/II/III) |
| Kidney | 0.633 ± 0.0617 | 46.7 | 81.0 | >32.9986 | 30 (I/II) |
| Lung | 0.643 ± 0.0381 | 54.1 | 73.0 | >31.181 | 108 (I/II/III/IV) |
| Normal | — | — | — | — | 100: 50F/50M |

*p < 0.0001

As can be seen in Table 6, the AUC (area under curve, a probability for screening cancer) value was measured at 0.941±0.0205 (mean±SEM), and the cut-off value at >33.8179 ng mL, with a sensitivity of 94.9% and a specificity of 82.0%.

This data indicates that thioredoxin 1 can be used as a breast cancer marker capable of discriminating breast cancer patients from the female normal control at a probability of about 95%, with superior sensitivity and selectivity.

4-2. Measurement of Serum Thioredoxin 1 Level in Patients with Breast Cancer and Other Cancers Thioredoxin 1 levels in blood samples, preferably serum samples obtained from patients with breast cancer (BC), lung cancer (LC), kidney cancer (KC) and colorectal cancer (CRC) were assayed using ELISA, and the results are shown in FIG. 9 and Table 5.

Figure 9:
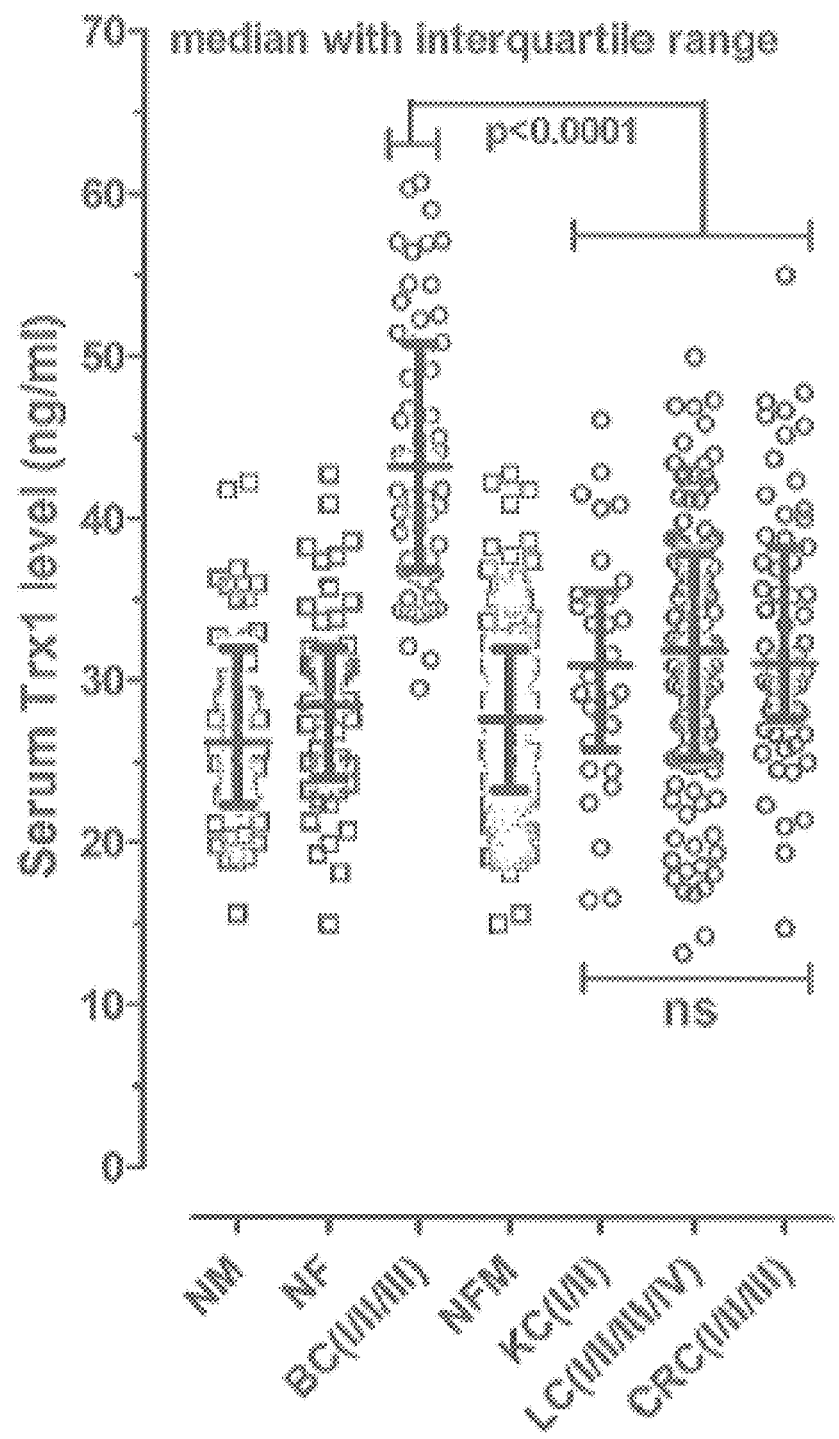
FIG. 9 shows serum thioredoxin 1 levels in the breast cancer group and other cancer groups (kidney cancer, lung cancer and colorectal cancer), as measured by ELISA.

As can be seen in FIG. 9, serum thioredoxin 1 levels were higher in the breast cancer group than in other cancer patients as well as in the female normal control (NF) and male normal control (NM), with statistical significance. Further, as show in Table 5, the blood of breast cancer patients retained significantly higher levels of thioredoxin 1 than did that of other cancer patients.

Figure 10:
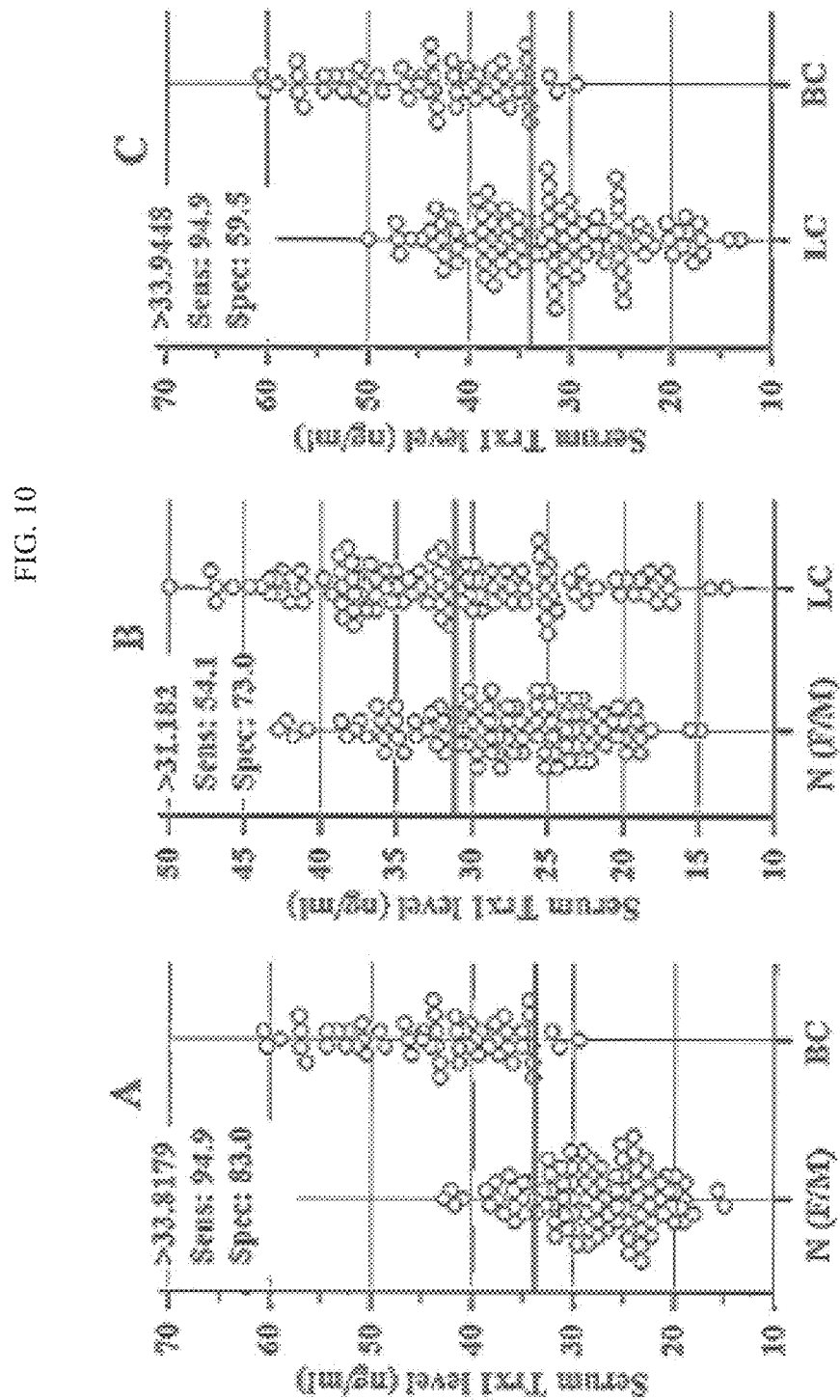
FIG. 10 shows the comparison of serum thioredoxin level between the breast cancer group and the lung cancer group.

(CRC)) was subjected to interactive dot diagram and ROC curve analysis, and the results are shown in FIG. 10 and Table 7.

TABLE 7

| Type of Cancer | AUC* (±SEM) | Sensitivity (%) | Specificity (%) | Trx1 Cut-off Value (ng/ml) |
| --- | --- | --- | --- | --- |
| BC/NMF | 0.947 ± 0.0155 | 94.9 | 33.0 | >33.8179 |
| BC/CRC | 0.831 ± 0.0365 | 94.9 | 60.3 | >33.5024 |
| BC/KC | 0.873 ± 0.0390 | 79.7 | 80.7 | >36.1850 |
| BC/LC | 0.842 ± 0.0295 | 94.9 | 59.5 | >33.9448 |

*p < 0.0001

As is understood from the data of FIG. 10 and Table 7, serum thioredoxin 1 levels were significantly higher in the breast cancer group than in other cancer patient groups as well as in the female and male normal control (NFM). In addition, when the serum thioredoxin 1 level was measured in breast cancer patients in comparison with other cancer patients, the AUC (area under curve) value exceeded 0.83, with the sensitivity and selectivity detected at more than 80% and 60%, respectively, in all cases, indicating that thioredoxin 1 is useful as a breast cancer-specific marker.

4-4. Comparison of Sensitivity Between Thioredoxin 1 and Antioxidant Proteins Serum levels of TXNDC1 (thioredoxin domain-containing protein 1) and Grx3 (Glutaredoxin 3), both of which belong to the thioredoxin superfamily and increase in expression level within cells in sensitive response to oxidative stresses, were compared to those of thioredoxin 1 in breast cancer patients, and the results are shown in FIG. 11.

Figure 11:
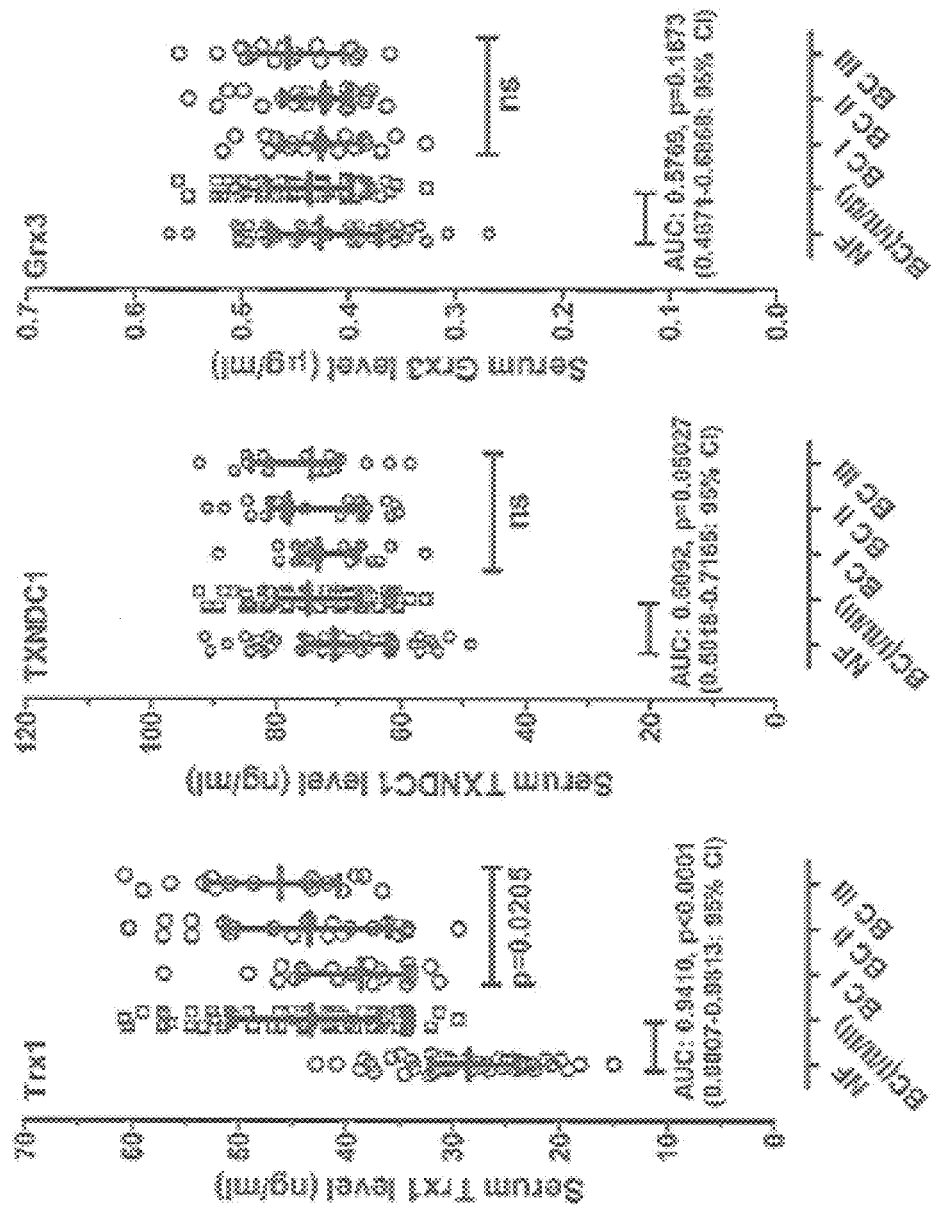
FIG. 11 shows serum levels of thioredoxin 1 and the antioxidant proteins TXNDC1 and Grx3 in the breast cancer group.

As shown in FIG. 11, increased serum levels of TXNDC1 and Grx3 were detected in breast cancer patients, but the levels were significantly lower than thioredoxin 1 levels. Further, TXNDC1 and Grx3 exhibited an AUC of less than 0.6. The serum thioredoxin 1 level was observed to have a proportional correlation with the progress of breast cancer, with statistical significance, whereas there were no significant correlations between the serum levels of TXNDC1 and Grx3 and the progress of breast cancer.

4-5. Sensitivity of Thioredoxin 1 with the Progress of Cancer

In order to reexamine the selectivity of thioredoxin 1 as a breast cancer-specific marker and to confirm the proportional correlation of serum thioredoxin 1 level with the progress of breast cancer, a comparison was made with blood samples taken from many lung cancer patients (LC). The results are shown in FIG. 12.

Figure 12:
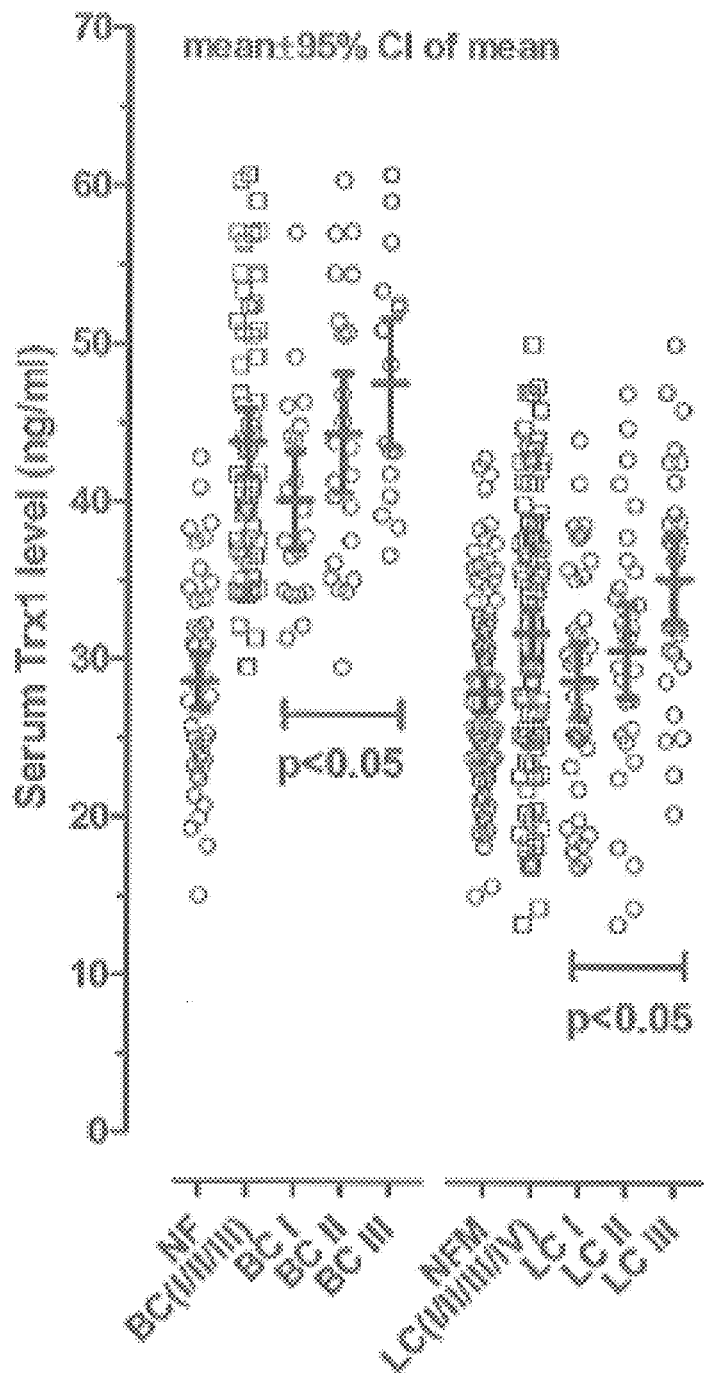
FIG. 12 shows changes of serum thioredoxin 1 level with the progress of breast cancer and lung cancer.

As can be seen in FIG. 12, the serum thioredoxin 1 level exhibited a correlation with the progress of breast cancer in a pattern similar to that shown in the progress of lung cancer.

This data indicates that the increase of serum thioredoxin 1 level with the progress of cancer is due to the oxidative stress increased with the progress of cancer. However, the serum thioredoxin 1 level in the lung cancer group was 35% lower than that in the breast cancer group, suggesting that the high increase in the breast cancer group is attributed to the specificity of thioredoxin 1 for breast cancer.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

---

We claim:

1. A method for diagnosing and treating breast cancer, comprising:
   (a) obtaining a blood sample from a subject and isolating a serum from the blood sample;
   (b) contacting the serum with an anti-thioredoxin 1 antibody;
   (c) measuring a concentration of thioredoxin 1 in the serum reacted with the anti-thioredoxin 1 antibody;
   (d) diagnosing the subject with stage I-III breast cancer based on the concentration of the thioredoxin 1 obtained from step (c), wherein the concentration of thioredoxin 1 is from 40.10±6.551 ng/mL to 47.53±7.695 ng/mL; and
   (e) treating the patient with an adjuvant therapy.

2. The method according to claim 1, wherein said determining the expression level of thioredoxin 1 comprises measuring a concentration of mRNA encoding thioredoxin 1 in the tissue or in the blood sample.

3. The method according to claim 1, wherein the subject is diagnosed with stage I breast cancer when the concentration of thioredoxin 1 is 40.10±6.551 ng/mL.

4. The method according to claim 1, wherein the subject is diagnosed with stage II breast cancer when the concentration of thioredoxin 1 is 44.36±8.727 ng/mL.

5. The method according to claim 1, wherein the subject is diagnosed with stage III breast cancer when the concentration of thioredoxin 1 is 47.53±7.695 ng/mL.

6. The method according to claim 1, wherein the concentration of thioredoxin 1 in the serum reacted with the anti-thioredoxin 1 antibody is measured using an ELISA test in step (c).

* * * * *